United States Patent
Hossack et al.

[11] Patent Number: 5,944,666
[45] Date of Patent: Aug. 31, 1999

[54] ULTRASONIC METHOD FOR IMAGING BLOOD FLOW INCLUDING DISRUPTION OR ACTIVATION OF CONTRAST AGENT

[75] Inventors: John A. Hossack, Palo Alto; Paul E. Chandler, Santa Cruz, both of Calif.

[73] Assignee: Acuson Corporation, Mountain View, Calif.

[21] Appl. No.: 08/916,163

[22] Filed: Aug. 21, 1997

[51] Int. Cl.⁶ ........................................... A61B 8/00
[52] U.S. Cl. ............................................. 600/458; 600/454
[58] Field of Search ..................................... 600/437, 454, 600/458, 463, 465

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,040,537 | 8/1991 | Katakura . |
| 5,111,823 | 5/1992 | Cohen . |
| 5,115,809 | 5/1992 | Saitoh et al. . |
| 5,135,000 | 8/1992 | Akselrod et al. . |
| 5,190,766 | 3/1993 | Ishihara . |
| 5,195,520 | 3/1993 | Schlief et al. . |
| 5,197,477 | 3/1993 | Peterson et al. . |
| 5,215,680 | 6/1993 | D'Arrigo . |
| 5,219,401 | 6/1993 | Cathignol et al. . |
| 5,233,994 | 8/1993 | Shmulewitz . |
| 5,255,683 | 10/1993 | Monaghan . |
| 5,287,753 | 2/1994 | Routh et al. . |
| 5,313,948 | 5/1994 | Murashita et al. . |
| 5,358,466 | 10/1994 | Aida et al. . |
| 5,380,411 | 1/1995 | Schlief . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,540,909 | 7/1996 | Schutt . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |

(List continued on next page.)

FOREIGN PATENT DOCUMENTS 0 357 164 of 0000 European Pat. Off. .
0 770 352 A1 5/1997 European Pat. Off. .

OTHER PUBLICATIONS

T.G. Leighton, "Transient excitation of insonated bubbles." Research Notes.

(List continued on next page.)

*Primary Examiner*—Marvin M. Lateef
*Assistant Examiner*—Ali M. Imam
*Attorney, Agent, or Firm*—Brinks Hofer Gilson & Lione

[57] ABSTRACT

An ultrasonic imaging system uses first and second perpendicular arrays. The first array is operated at high power to selectively destroy contrast agent suspended in flowing blood in discrete regions. The second array is used to image the alternating bands of contrast agent depleted blood and contrast image containing blood in order to allow blood flow characteristics to be assessed.

25 Claims, 6 Drawing Sheets

U.S. PATENT DOCUMENTS

| | | |
|---|---|---|
| 5,617,862 | 4/1997 | Cole et al. . |
| 5,628,322 | 5/1997 | Mine . |
| 5,632,277 | 5/1997 | Chapman et al. . |
| 5,678,554 | 10/1997 | Hossack et al. . |
| 5,696,737 | 12/1997 | Hossack et al. . |
| 5,724,976 | 3/1998 | Mine et al. . |
| 5,732,707 | 3/1998 | Widder et al. . |
| 5,735,281 | 4/1998 | Rafter et al. . |
| 5,740,807 | 4/1998 | Porter . |

OTHER PUBLICATIONS

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Marc Gensane, "Bubble population measurements with a parametric array." 1994 Acoustical Society of America, 95(6) Jun.

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Shmuel Gottlieb, M.D. et al., "Effect of Pressure on Echocardiographic Videodensity from Sonicated Albumin: An In Vitro Model." J. Ultrasound Med. 14 (1995).

J.W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 224.

Chiang C. Mei, et al., "Parametric resonance of a spherical bubble." J. Fluid Mech. (1991) vol. 229.

V.L. Newhouse, et al., "Bubble size measurements using the nonlinear mixing of two frequencies." J. Acoust. Soc. Am. 75(5), May 1984.

Janet B. Jones–Oliveira, et al., "Transient fluid—solid interaction of submerged spherical shells revisited: Proliferation of frequencies and acoustic radiation effects." Acoustical Society of America, 96(2) Pt. 1, Aug. 1994.

Chandra M. Sehgal, PhD., et al., "Sonographic Enhancement of Renal Cortex by Contrast Media." J. Ultrasound Med, 14 (1995).

"Abstract Session IV Contrast and Ischemia" and "Poster Session A New Technologies." Journal of the American Society of Echocardiography, vol. 8, No. 3, May 1995.

Chandra M. Sehgal, PhD, et al., "Influence of Postprocessing Curves on Contrast—Echographic Imaging: Preliminary Studies." J. Ultrasound Med, 14 (1995).

Deborah J. Rubens, M.D., et al., "Sonoelasticity Imaging of Prostate Cancer: In Vitro Results." Radiology, vol. 995, No. 2, 1995.

Kotaro Sato, et al., "Numerical analysis of a gas bubble near rigid boundary in an oscillatory pressure field." J. Acoustical Society of America, 95(5), May 1994.

L.W. Anson et al., "Ultrasonic scattering from spherical shells including viscous and thermal effects." J. Acoustical Society of America, 93(4), Apr. 1993.

B. Schrope, et al., "Simulated Capillary Blood Flow Measurement Using A Nonlinear Ultrasonic Contrast Agent," Ultrasonic Imaging 14 (1992).

Fred Lee, Jr., M.D., et al., "Sonoelasticity Imaging: Results in in Vitro Tissue Specimens." Radiology, vol. 181, No. 1, 1991.

Kevin J. Parker, PhD, et al., "Sonoelasticity of Organs: Shear Waves Ring a Bell." J. Ultrasound Med., 11 (1992).

William Armstrong, M.D., et al., "American Society of Echocardiography Position Paper on Contrast Echocardiography." draft 1'Jun. 6, 1994.

K.J. Parker, et al., "Tissue Response to Mechanical Vibrations for 'Sonoelasticity Imaging'." Ultrasound in Med. & Biol., vol. 16, No. 3, (1990).

Robert M. Lerner, et al., "'Sonoelasticity' Images Derived from Ultrasound Signals in Mechanically Vibrated Tissues." Ultrasound in Med. & Biol., vol. 16, No. 3, (1990).

J. Ophir, et al., "Elastography: A Quantitative Method for Imaging the Elasticity of Biological Tissues." Ultrasonic Imaging 13 (1991).

J.A. Hossack et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document, 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology" American College of Cardiology, 45th Annual Scientific Session, Mar. 24–27, 1996 pp. 21A, 63A, 239–240A.

Yang–Sub Lee, et al., "Time domain modeling of pulsed finite–amplitude sound beams." 1995 Acoustical Society of American, 97(2), Feb. 1995.

Michalakis A. Averkiou, et al., "Self–demodulation of amplitude–and frequency–modulated pulses in a thermoviscous fluid." J. Acoustical Society of America, 94(5), Nov. 1993.

Nico de Jong, "Physical Properties and Technical Aspects of Ultrasound Contrast Agents." (one page).

"Small Spheres Lead to Big Ideas."Research News, Science vol. 267, Jan. 20, 1995.

Excerpt frpm Ultrasonics: Fundamentals and Applications (1992), pp. 380–393, 363–365.

ULTRASONIC METHOD FOR IMAGING BLOOD FLOW INCLUDING DISRUPTION OR ACTIVATION OF CONTRAST AGENT

BACKGROUND OF THE INVENTION

This invention relates to ultrasonic imaging techniques for measuring blood flow parameters, such as velocity, flow volume, and turbulence.

Ultrasonic imaging systems have in the past been used to assess blood flow, typically by use of Doppler techniques. True blood velocity can only be determined with Doppler techniques if the Doppler incidence angle can be determined. Additionally, flow volume is difficult to derive without making sweeping assumptions about the relation between the two-dimensional image of a blood vessel and its cross sectional dimension. Such assumptions are best made with the aid of three-dimensional imaging or other out-of-plane imaging techniques, which are often not available.

It is also known that second harmonic contrast agents can be used to enhance ultrasonic imaging of blood flow. See, for example, Uhlendorf U.S. Pat. No. 5,410,516 and Johnson U.S. Pat. No. 5,456,257. It is known that a pressure of approximately 2 MPa will destroy contrast agent such as conventional micro-bubbles, and that a much lower pressure of approximately 0.2 MPa is sufficient to produce a second harmonic response from these contrast agents for imaging purposes. Contrast agents are available commercially under the trademarks EchoGen (Sonus Pharmaceuticals, Bothell, Wash.), Optison FS069 (Molecular Biosystems Inc., San Diego, Calif.), and Levovist (Schering AG, Germany). It is customary when using harmonic imaging systems with non-linear contrast agents to manage the transmitted ultrasonic power level or pulse repetition rate so as not to destroy contrast agent bubbles excessively.

SUMMARY OF INVENTION

The present invention is defined by the following claims, and nothing in this section should be taken as a limitation on those claims. By way of introduction, the preferred embodiments described below combine higher power, intermittently transmitted ultrasonic signals with interspersed lower power transmitted ultrasonic signals. The higher power signals are confined to a relatively small portion of the region imaged with the lower power signals, and the higher power signals destroy or otherwise disrupt contrast agent in this region. Images derived from echo information related to the second, lower power transmitted ultrasonic signals are then used to track the movement and mixing of the regions of blood depleted of operative contrast agent by the higher power ultrasonic signals. In this way, blood flow velocity, turbulence and velocity profiles can all be assessed.

DETAILED DESCRIPTION OF THE PRESENTLY PREFERRED EMBODIMENTS

Figure 1:
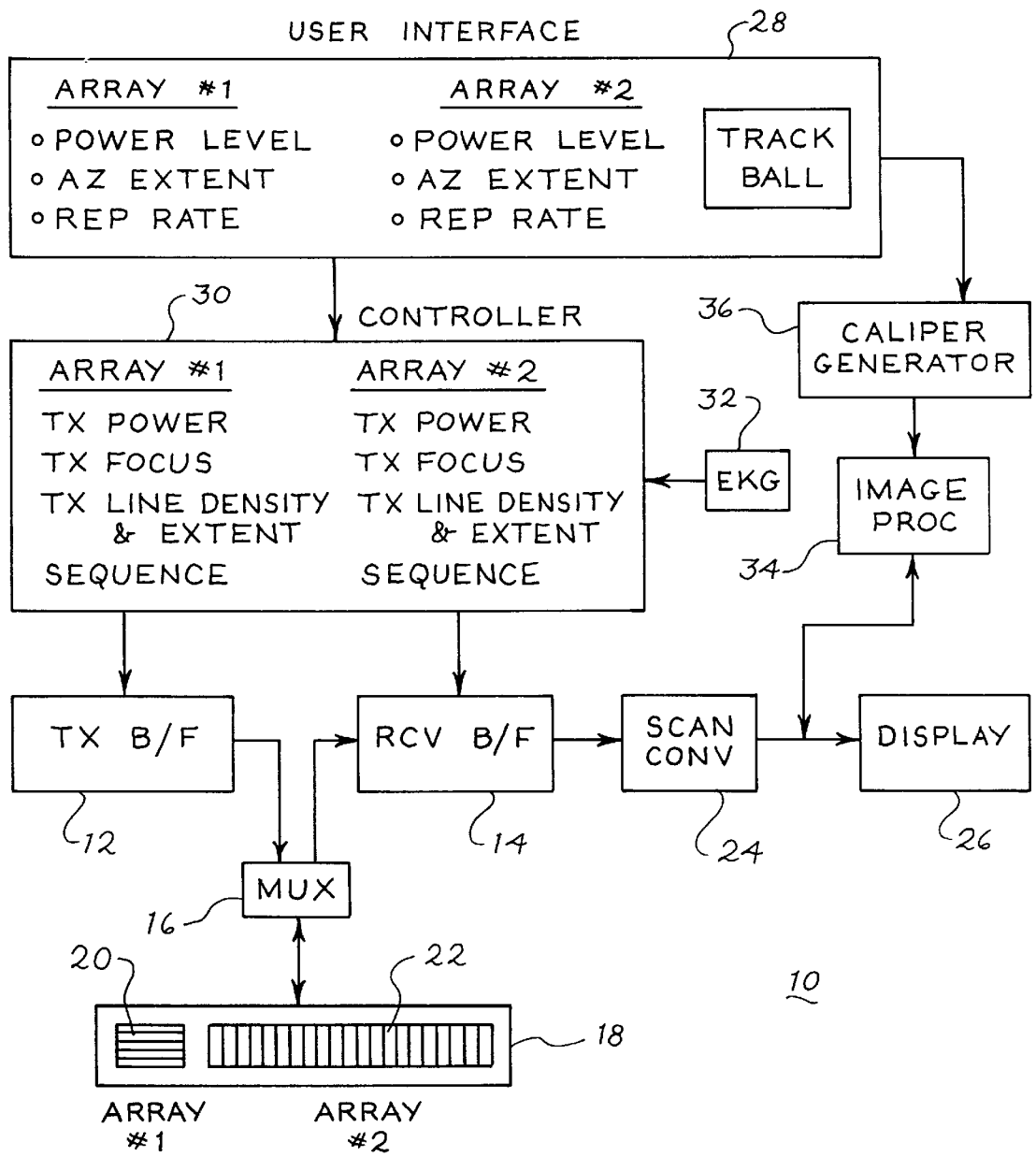
FIG. 1 is a block diagram of an ultrasonic imaging system suitable for use with this invention.

Turning now to the drawings, FIG. 1 shows a block diagram of an ultrasound imaging system 10 that is suitable for use with this invention. The system 10 includes a transmit beamformer 12 and a receive beamformer 14 that are connected via a multiplexer 16 to a transducer probe 18. In this case the transducer probe 18 includes a first transducer array 20 and a second transducer array 22 that are oriented preferably but not necessarily at right angles to one another as shown. The transducer beamformer 12 includes controlled power amplifiers on output, and the receive beamformer 14 includes conventional protection circuits, preamplifiers, and time varying gain amplifiers on receive. The transmit beamformer 12 supplies ultrasonic transmit signals via the multiplexer 16 selectively to the arrays 20, 22, which respond by transmitting ultrasonic power into the tissue adjacent the arrays 20, 22. Ultrasonic echoes associated with transmitted ultrasonic signals are received by the array 22 and formed into receive beams by the receive beamformer 14. These receive beams are processed via a scan converter 24 for display on a display 26. The elements of the system 10 described above are conventional, and can be implemented using well known elements of the prior art. Preferably, the receive beamformer 14 is of the type capable of creating multiple receive beams per transmit event to improve lateral resolution for a limited number of transmit events. See for example, the receive beamformer described in U.S. patent application Ser. No. 08/432,615, filed May 2, 1995 and assigned to the assignee of the present invention. In this way the potentially destructive transmitted ultrasonic energy needed for imaging can be reduced.

The ultrasonic imaging system 10 includes a user interface 28 that allows the user to manually select power level, azimuthal beam extent and/or spacing, and repetition rate separately for the first and second arrays 20, 22. The user interface 28 also includes a track ball that can be used to position a cursor to designate selected points of the displayed images as described below. The user interface 28 supplies control signals to a controller 30. The controller 30 selects transmit power, transmit focus, transmit line density, azimuthal beam extent and/or spacing, and transmit sequence separately for the first and second arrays 20, 22, and applies this information to the transmit beamformer 12. As described below, the transmit beamformer 12 is alternately controlled by the controller 30 in response to the user interface 28 to fire the first array 20 at higher power levels and the second array 22 at lower power levels.

Figure 2:
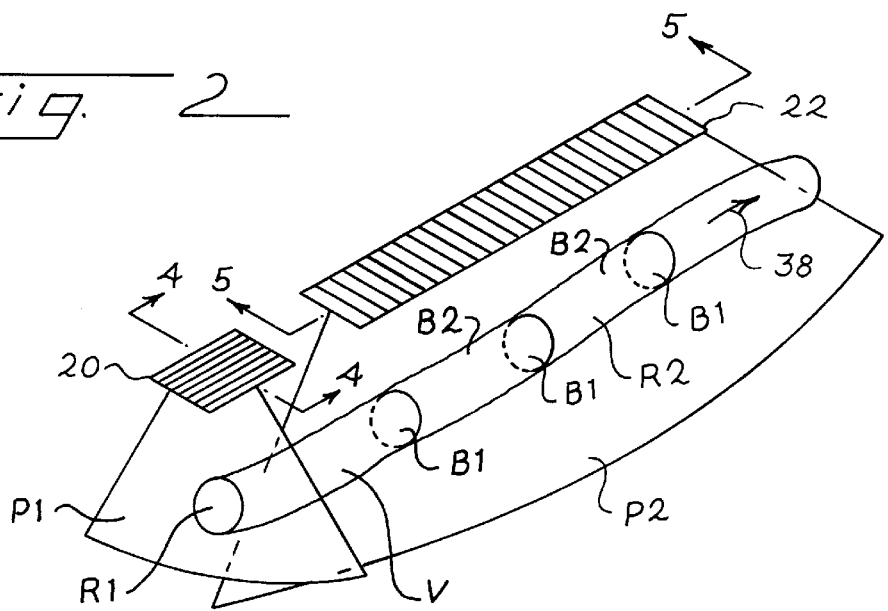
FIG. 2 is a schematic perspective view of the transducers of FIG. 1 in use.

FIG. 2 provides a perspective view of the first and second arrays 20, 22 as used to image blood flow in a vessel V. As shown in FIG. 2, the arrays 20, 22 are provided with respective scan planes P1, P2, and the scan planes P1, P2 are preferably but not necessarily oriented perpendicularly to one another. The scan plane P1 of the first array 20 is oriented to cross the vessel V, and the intersection between the vessel V and the scan plane P1 forms a first region R1. The second transducer array 22 is characterized by a second scan plane P2 that is oriented to extend along the length of the vessel V. The first and second scar planes P1, P2 may intersect so that an image formed using the second array 22 observes the region being insonified in the scan plane P1 with the first array 20. In FIG. 2 the arrow 38 designates blood flow velocity vector in the vessel V, and the region R2 of the vessel V in the scan plane P2 associated with the second transducer array 22 is positioned downstream of the region R1 with respect to blood flow velocity.

Figure 3:
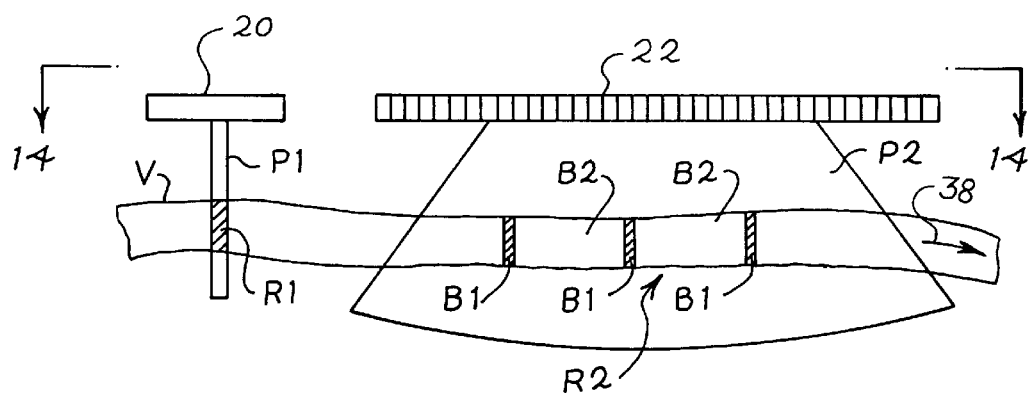
FIG. 3 is a side view of the transducers of FIG. 2.
Figures 4, 5:
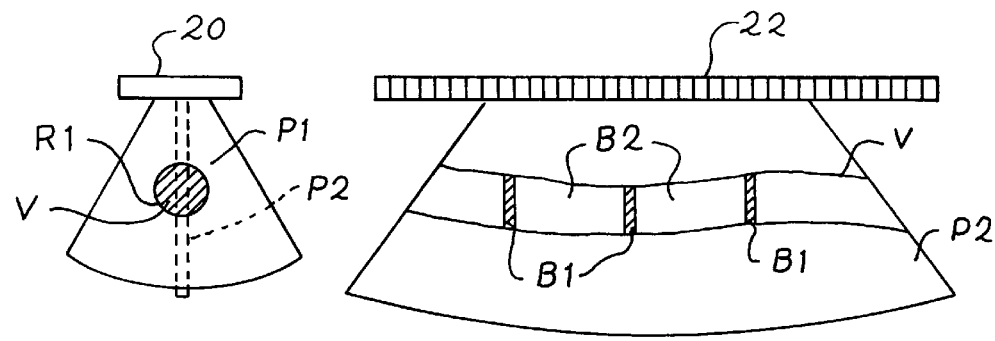
FIG. 4 is a cross-sectional view taken along line 4—4 of FIG. 2.
FIG. 5 is a cross-sectional view taken along line 5—5 of FIG. 2.

FIG. 3 is a side view clarifying the geometry illustrated in FIG. 2. FIG. 3 clearly shows that the scan plane P1 is perpendicular to the scan plane P2. FIGS. 4 and 5 are sectional views taken in the scan plane P1 (FIG. 4) and in the scan plane P2 (FIG. 5).

As shown in FIGS. 2–5, the transmit beamformer described above transmits at selected time intervals high intensity ultrasound signals in the scan plane P1. The power level of these high intensity ultrasound signals is chosen to be sufficient to disrupt or destroy contrast agent included in the blood in the region R1. For example, a sweep of single acoustic beams (in the conventional swept-beam format) can be used. If desired, the sweep of acoustic beams can be performed at an unusually high firing rate, because in this embodiment no images are collected from echo information associated with the high intensity ultrasound signals transmitted via the first array 20. For this reason, interference between reflected signals from an earlier beam arising from a greater range and reflected signals from a later beam arriving from a shorter range is not a concern. Preferably, the user can limit the azimuthal spread of the high intensity ultrasound sweep so that it covers the vessel V but does not waste excessive time scanning beyond the azimuthal extent required to substantially destroy contrast agent in the region R1. If desired, within a single set of high intensity ultrasound signals multiple firings across the entire plane or individual lines with different focal depths may be allowed to ensure that contrast agent is destroyed throughout the region R1.

Because the transducer array 20 is fired intermittently, the result is an alternating sequence of bubble-depleted regions B1 (in which the contrast agent has been depleted or disrupted) separated by bubble-loaded regions B2 (in which the contrast agent retains its original concentration). As the blood flows through the vessel V these regions B1, B2 move axially along the vessel downstream of the scan plane P1.

This motion of the bubble-loaded regions B2 and the bubble-depleted regions B1 is monitored in the scan plane P2 with the array 22. Preferably, the array 22 is operated at a substantially lower ultrasound power level than the array 20, such that the array 22 images contrast agent substantially without destroying it. The contrast agent may be monitored in either a fundamental imaging mode or a harmonic imaging mode. If a harmonic mode is used, the array 22 is preferably operated at a sufficiently high power level to activate a second harmonic response from the contrast agent, and the repetition rate of the array 22 is preferably kept at a low level to minimize destruction of the contrast agent. As shown in FIGS. 3 and 5, the vessel V when imaged in the plane P2 will appear mostly filled with regions B2 containing operative contrast agent, with low intensity lines in the regions B1 in which the contrast agent was disrupted by the high power ultrasonic signals from the array 20.

When non-linear contrast agent is used the transmit beamformer is operated to selectively transmit ultrasonic power near a fundamental frequency while suppressing the transmission of ultrasonic power at the desired harmonic, and the receive beamformer is operated to selectively receive and process echo information near the harmonic frequency, while suppressing echo information at the fundamental frequency.

Because the ultrasonic power intensities for the arrays 20, 22 are preferably under user control, the user can set the power level for the array 20 high enough to destroy contrast agent in the plane P1 and the power level for the array 22 low enough to allow useful imaging in the plane P2. Because the user preferably controls the pulse repetition rate of ultrasonic signals applied to the first array 20, the user can ensure that the bubble-depleted regions B1 are suitably spaced. Different vessels and different individuals have different blood flow rates, and for this reason the optimal pulse repetition rate will vary depending on the application.

The spacing of the regions B1 along with knowledge of the firing interval used for the array 20 may be used to measure blood velocity in the blood vessel V with reduced angle dependence. The relative spacing of the regions B1 provides information about the time history of the blood velocity, i.e. a close spacing between adjacent regions B1 corresponds to low blood velocity and a large spacing between adjacent regions B1 corresponds to high blood velocity (e.g. near systole).

Figure 6:
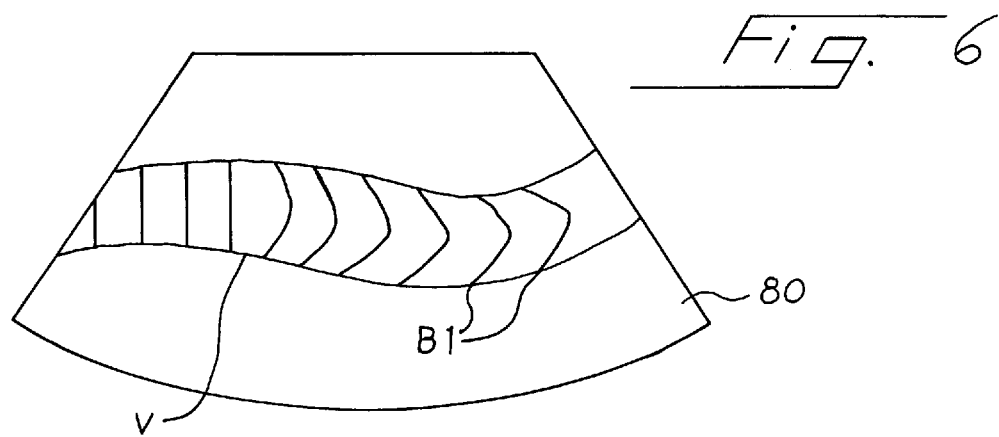
FIG. 6 is a schematic view of an ultrasonic image formed with the system of FIG. 1.

FIG. 6 shows an image 80 taken with the array 22 of FIG. 1. As shown in FIG. 6, the regions B1 of blood depleted of contrast agent distort to an increasing extent as they move downstream due to the fact that blood flows faster in the center of the vessel than at the edges of the vessel. The degree of bending of the regions B1 is an indication of variations in velocity across the diameter of the blood vessel. Additionally, the regions B1 fade as the bubble-saturated blood remixes with the bubble-depleted blood. The speed of this remixing can be used as an indication of blood flow turbulence. Further, evidence of flow eddies may appear on the display. Such turbulence is of particular interest in the vicinity of vessel bifurcations and regions of stenosis, if such regions exist.

Figure 7:
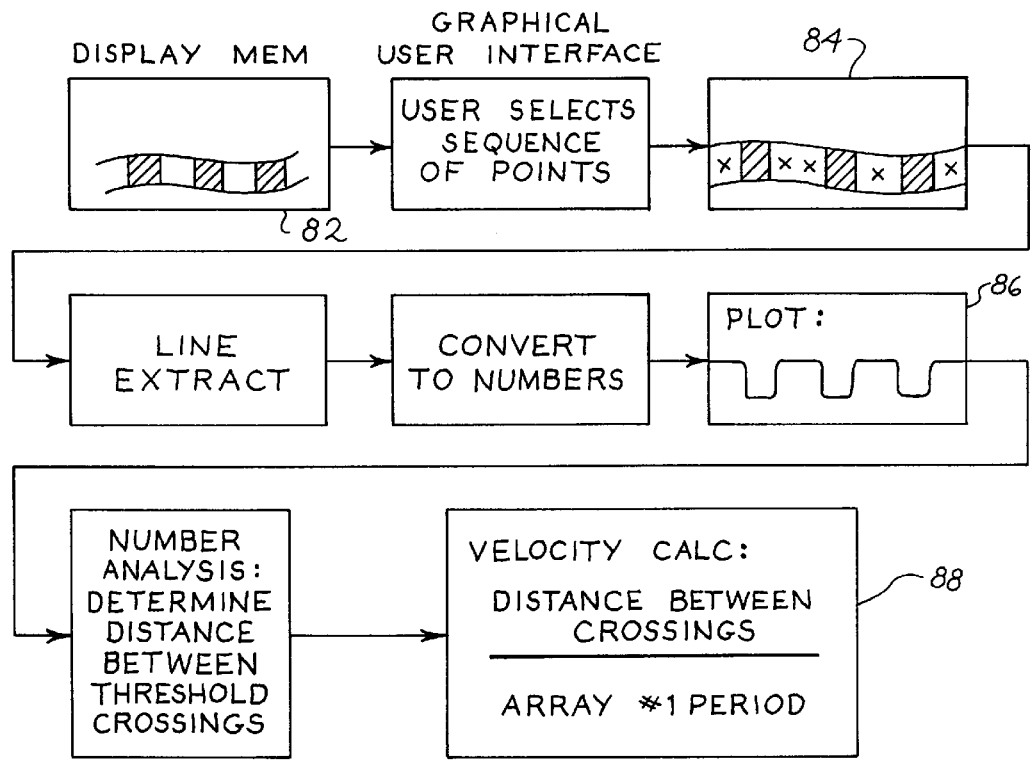
FIG. 7 is a flow diagram illustrating operation of the image processor of FIG. 1.

FIG. 7 is a flow diagram illustrating operation of the image processor 34 of FIG. 1. As shown in block 82, the image processor has access via a display memory to an image showing alternating bands of light (contrast agent bearing) blood and dark (contrast agent depleted) blood. A graphical user interface is then used to allow a user to select a sequence of points extending along the length of the vessel. Typically, the user selects a freeze frame mode of operation while measurements are being made. The image processor then develops a straight line extending through the user-designated points. Image intensity along this line is then converted to a digital sequence, which can be plotted as shown at 86. A selected threshold is applied to this plot to determine via numeral analysis the distance between threshold crossings. Blood flow velocity can then be calculated by dividing the distance between two adjacent crossings by the period between consecutive sets of firings of the first array 20.

Typically, blood velocity is greater in the center of a vessel than at the sides. Often, the velocity profile across a diameter of a vessel is generally parabolic in shape. For this reason, a more accurate measure of average blood velocity or blood volumetric flow may be determined by repeating the above-described velocity measuring process at several distances from the central axis of the vessel. The volume of blood flow associated with each velocity measurement is integrated around the central axis to find flow associated with an annulus of blood around the axis. This process is repeated for several different distances from the axis, and the flows from the annulli are summed or integrated to calculate the total vessel flow.

Figure 8:
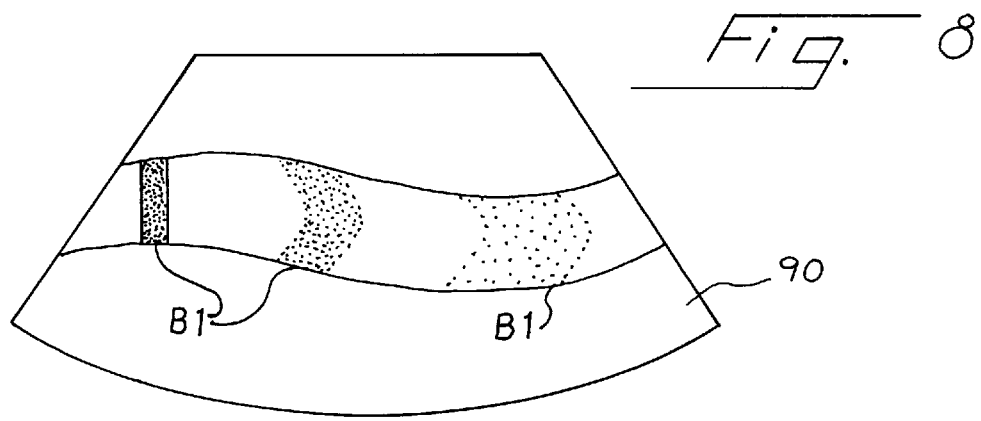
FIG. 8 is a schematic view of another image formed with the system of FIG. 1.
Figure 9:
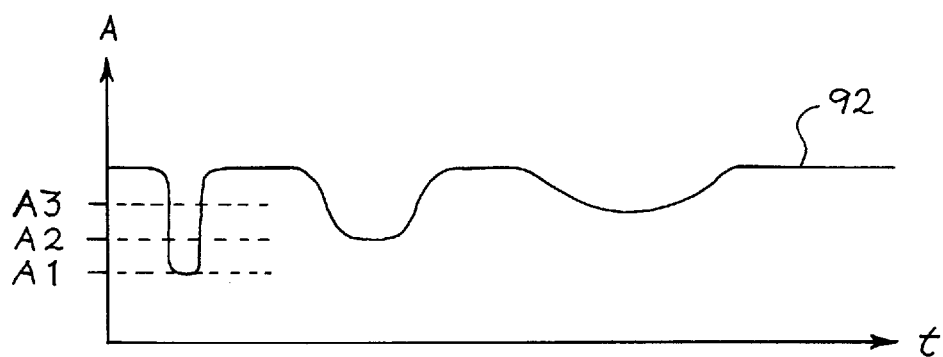
FIG. 9 is a graph of amplitudes of the image of FIG. 8.

FIG. 8 shows another image 90 formed with the system of FIG. 1. In the image 90 the regions B1 are shown to increase in length, as the contrast agent depleted blood mixes with the contrast agent containing blood. Using techniques similar to those described above in conjunction with FIG. 7, the image processor can form a curve 92 as shown in FIG. 9 showing intensity of the image along the centerline of the vessel. Then the depths 3, A2, and A3 of the troughs associated with three consecutive regions B1 can be measured, and the rate of change of the trough depth used as a measure of blood flow turbulence.

Figure 10:
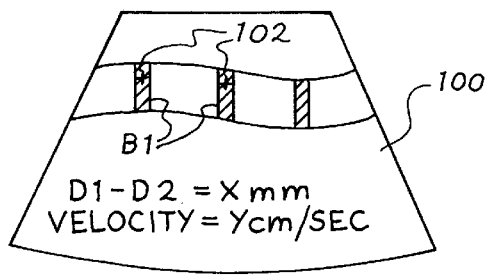
FIG. 10 is a schematic view of another image generated by the system of FIG. 1, showing user-positioned calipers.

As shown in FIG. 10, the caliper generator 36 of FIG. 1 can be used to position cursors 102 at two adjacent regions B1. Since the pulse repetition rate is known within the system 10, the blood velocity may automatically be calculated based on the caliper distance and the pulse repetition interval. The image processor is programmed to display the distance D1–D2 associated with the first and second calipers and the calculated velocity based on this distance. Strictly, this velocity only applies to the specific region of the vessel that has been selected for measurement.

Figure 11:
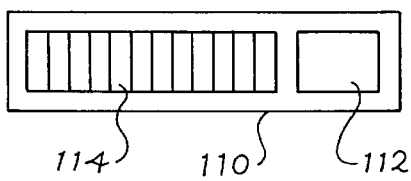
FIGS. 11 and 12 are plan views of two alternative transducer probes suitable for use of the system of FIG. 1.
Figure 12:
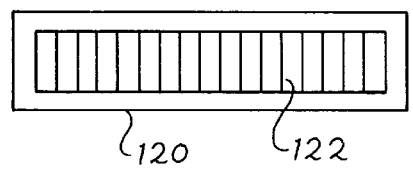

As shown in FIGS. 11 and 12, it is not required in all embodiments that first and second arrays 20, 22 as shown in FIG. 1 be used. As shown in FIG. 11, a transducer probe 110 can be used having a first transducer 112 which is used to destroy contrast agent. In this case the transducer 112 is a single element transducer that is convexly shaped to focus transmitted power in the desired plane. In this embodiment a second transducer array 114 similar to the array 22 of FIG. 1 is also included in the probe 110.

Figure 13:
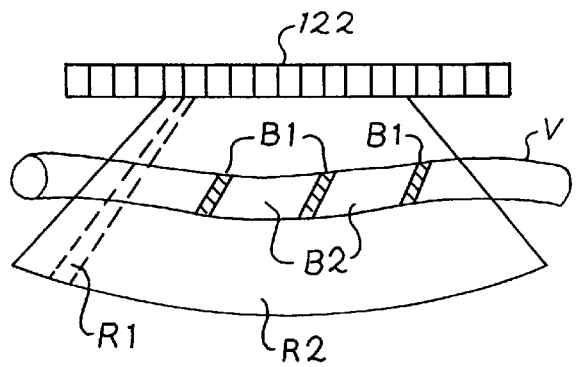
FIG. 13 is a schematic view showing the transducer probe of FIG. 12 in use.

As shown in FIG. 12, in another embodiment the transducer probe 120 can be used. The transducer probe 120 includes only a single transducer array 122. As shown in FIG. 13, different acoustic lines generated by the transducer array 122 are provided with different ultrasonic power levels. For example, within a single frame acoustic lines in the region R1 can be fired at a high power level to selectively disrupt contrast agent in the vessel V, while acoustic lines in the region R2 may be fired at a lower ultrasonic power level which is sufficient to image contrast agent without destroying it. In this case the regions R1, R2 may be included within a single frame of acoustic lines generated with the transducer array 122. In FIG. 13 the region R1 is situated near one edge of the frame, typically the upstream edge.

Other alternatives for the probe 18 are possible. For example, any of the transducer arrays described above may be one dimensional arrays, 1.5 dimensional arrays, or two dimensional arrays, using any desired transducer element shape, including plano-concave transducer elements and modified plano-concave transducer elements having a non-circular curvature.

When a transverse array such as the array 20 is used, it is preferable to use an array that provides a narrow beam in elevation to form a uniformly wide region B1 in which the blood is depleted of contrast agent. Preferably, a 1.5 D array is used. The elevation focus of this array is selected to correspond with the center of the vessel of interest. If desired, multiple transmit firings at a group of focal ranges in the vicinity of the vessel axis may be used. Alternately, an array with improved elevation beam profile, such as that described in Hanafy U.S. Pat. No. 5,415,175 or U.S. patent application Ser. No. 08/675,412, filed Jul. 2, 1996 (both assigned to the assignee of the present invention) can be used. In the event the beam from the transverse array 20 has a wider beam width than is desired, it is preferable that measurements between successive contrast agent depleted regions be made with respect to the centers of the depleted regions, or alternately at regions having the narrowest widths, if these regions correspond to the portion of the vessel which is of interest.

As another alternative, at least some of the firings of the first array 20 may be triggered from an EKG signal generated by the EKG signal generator 32 of FIG. 1. With this arrangement blood flow rate per heart beat can be derived, since the distance between depleted regions B1 can be measured, and the regions B1 can be synchronized with the heartbeat. In practice, the distance blood flows between successive heart beats will often be too great to be visible in a single ultrasound frame. For this reason, it will often be preferable to use multiple firings within a single heartbeat cycle such that the distance of blood flow within that cycle can be calculated from the sum of motions between the depleted regions occurring within the heart cycle. Also, the cross-sectional area of the blood vessel V can be conveniently measured by using an image formed with the transverse array 20, as described in detail in U.S. patent application Ser. No. 08/736,048 filed Oct. 22, 1996, assigned to the assignee of the present invention.

If desired, the first array 20 can be operated with a relatively large time spacing between adjacent lines within a single frame in order to cause the region of disrupted contrast agent to be positioned at an angle with respect to the scan plane P1. This will be explained in conjunction with FIGS. 14–25.

Figure 14:
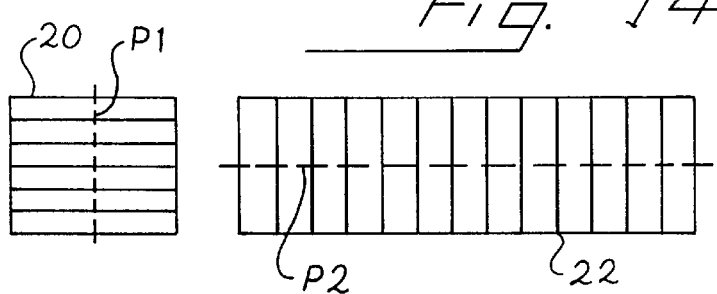
FIGS. 14, 15, 16 and 18 are schematic views illustrating one mode of operation of the embodiment of FIG. 3.

FIG. 14 is a schematic top view of the transducer arrays 20, 22 showing the orthogonal scan planes P1, P2. The orientation of FIG. 14 can best be understood by reference to FIG. 3, which defines the plane of FIG. 14. FIGS. 15, 16, 18, 20, 22 and 24 are positioned in the same orientation as FIG. 14, and the scan planes P1, P2 are shown for orientation purposes.

Figure 15:
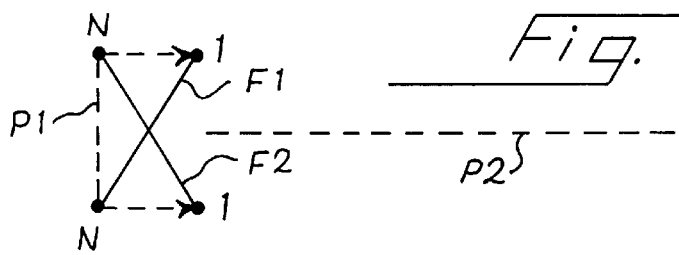

As shown in FIG. 15, in one alternative embodiment two relatively high power ultrasonic frames are fired simultaneously, each frame made up of transmit beams positioned in the scan plane P1. Multibeam transmit beamformers are known in the art. A preferred multibeam beamformer is described in U.S. patent application Ser. No. 08/673,410, filed Jul. 15, 1996 and assigned to the assignee of the present invention.

Figure 16:
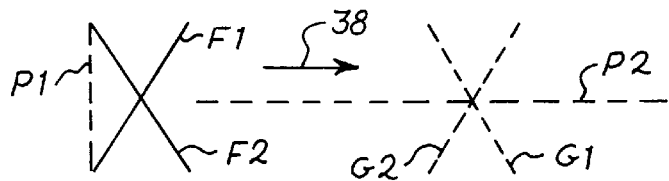
Figure 18:
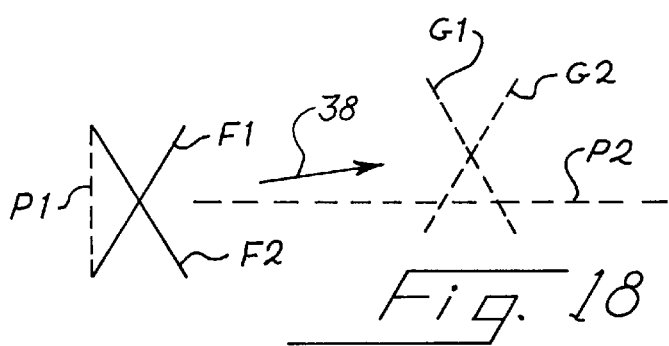

In FIG. 15 the first line to be fired in each frame is indicated by the reference symbol 1, and the last line to be fired in each frame is indicated by the reference symbol N. Though all of the lines 1-N are fired in the scan plane P1, blood flow causes the regions of disrupted contrast agent to travel downstream during the time required to fire the entire frame. Thus, by the time the Nth line is fired in the two simultaneous frames, the actual spatial distribution of the region of disrupted contrast agent takes the form of two crossed planes F1, F2 as shown in FIG. 15. For example, assuming that N=50, that the blood velocity is two centimeters per second, and that the width of each frame along the scan plane P1 is one centimeter, the elapsed time between the first and fiftieth beam within a frame can be chosen such that the offset between the spatial position of the first line and the fiftieth line is 4 millimeters. This is produced by firing the frame of 50 lines in the scan plane P1 slowly, over an interval of 0.2 seconds in this example. Thus, the delay between adjacent lines of the frame is 0.004 seconds. In FIGS. 15, 16 and 18, the reference symbols F1 and F2 will be used to designate the angled frames created as described above, corresponding to the regions of disrupted contrast agent.

Figure 17:
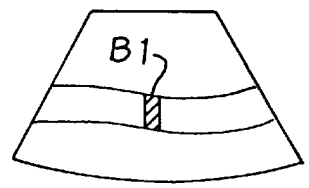
FIGS. 17 and 19 are schematic views of images formed during the modes of operation illustrated in FIGS. 16 and 18, respectively.

As shown in FIG. 16, in the event the scan plane P2 is closely aligned with the blood flow velocity vector 38, then the point of intersection of the propagated regions G1, G2 of disrupted contrast agent is located approximately at the scan plane P2. This arrangement results in an image in the scan plane P2 as shown in FIG. 17, in which a single region B1 of disrupted contrast agent is displayed.

Figure 19:
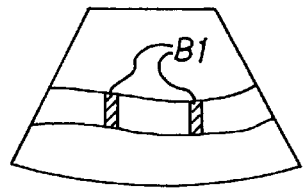

In the event the blood flow velocity vector 38 is not aligned with the scan plane P2, as shown in FIG. 18, then the propagated regions G1, G2 of disrupted contrast agent will separately intersect the scan plane P2. This geometry results in an image as shown in FIG. 19, in which there are two separate regions B1 of disrupted contrast agent. Thus, the number and separation of the regions B1 associated with a single set of firings of the transducer 20 guide the user to place the observation scan plane P2 most accurately in alignment with the blood flow velocity vector. As apparent in FIGS. 16 and 18, the greater the misalignment of the scan plane P2 with respect to the blood flow velocity vector 38, the greater the separation between the regions B1 of disrupted contrast agent.

Figure 20:
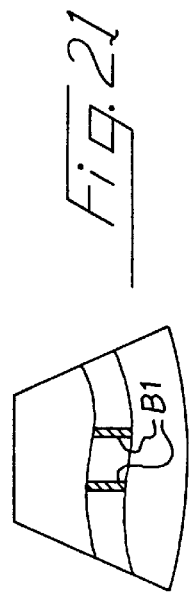
FIGS. 20, 22 and 24 are schematic views showing alternative modes of operation of the embodiment of FIG. 3.
Figure 21:
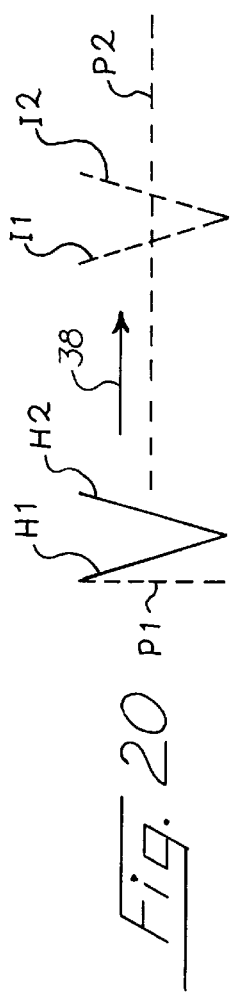
FIGS. 21, 23 and 25 are schematic views of displays formed during the modes of operation of FIGS. 20, 22 and 24, respectively.
Figure 22:
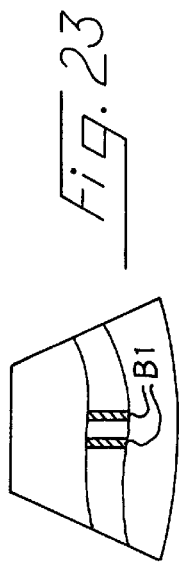
Figure 23:
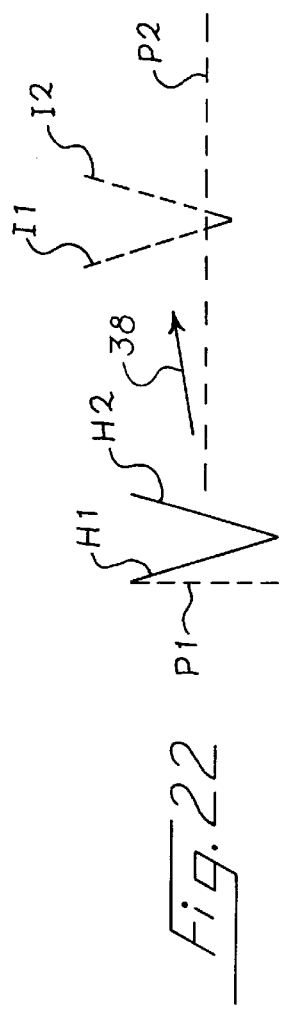
Figure 24:
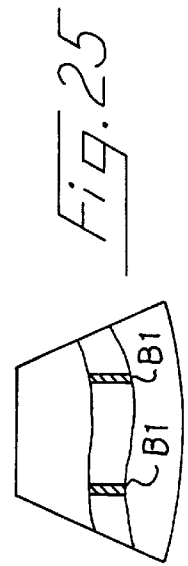
Figure 25:
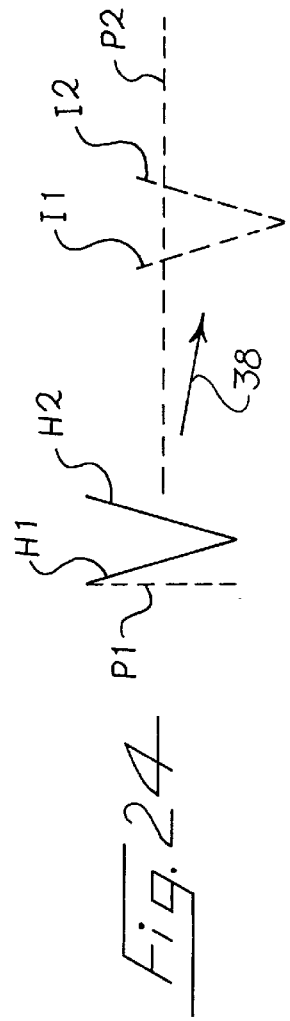

As shown in FIGS. 20 through 25, another alternative approach is to use two frames H1, H2 which are ancled to form a "V" rather than an "X" as described above. As shown in FIG. 20, when the scan plane P2 is oriented parallel to the blood flow velocity vector 38, a characteristic spacing is obtained between the lines of intersection between the propagated regions of disrupted contrast agent 11, 12 and the scan plane P2. This results in a characteristic desired spacing between adjacent regions B1 of disrupted contrast agent. As shown in FIGS. 22 and 23, when the scan plane P2 is positioned to one side of the blood flow velocity vector 38, the characteristic spacing between the regions B1 is reduced, and conversely when the scan plane P2 is angled in the opposite direction with respect to the blood flow velocity vector 38, the regions B1 are increased in separation. The advantage of the arrangement of FIGS. 20 through 25 is that if the blood flow velocity vector is offset with respect to the scan plane P2, the user is guided as to the direction in which the scan plane P2 must be shifted in order to achieve the desired alignment with the blood flow velocity vector.

In the foregoing examples, the contrast agent has been disrupted in relatively small portions of the blood, thereby creating darker planes which are characterized by disrupted contrast agent. Another alternative form of the invention utilizes a much larger duty cycle for the contrast agent disrupting beam generated as described above. For example, relatively high energy ultrasound signals may be formed with a duty cycle of greater than 50%, as for example for 90 or 99% of the available time, so that only occasional regions of operative contrast agent remain. If this approach is used, occasional white lines of highly reflective contrast agent will be imaged and the majority of the imaged blood will appear as dark regions, because the contrast agent has been disrupted in these regions. With this approach line interleaving may be preferable between individual transmit events in the two scan planes P1, P2. From this discussion it should be apparent that the present invention can be implemented with a wide variety of duty cycles for the high intensity ultrasound signals in the scan plane P1. This duty cycle can range as desired to as low as 1% or lower, and to as great as 99% or greater. In general, when the duty cycle is less than 50%, the majority of the contrast agent will remain operative, while when the duty cycle is greater than 50% the majority of the contrast agent will be disrupted.

As yet another alternative, the present invention can be used with contrast agent of the type described in Katakura U.S. Pat. No. 5,040,537. Contrast agent of this type is characterized by very small microbubbles, which are often about 2 microns in diameter and are invisible to a conventional ultrasound beam. When a high power ultrasound beam is applied to such contrast agent, larger microbubbles appear which are echogenic. At present it is not entirely understood how these larger bubbles are created by an ultrasound beam; one alternative proposed mechanism includes the destruction of the original very small microbubbles and subsequent gas agglomeration. Another possible mechanism is that the original microbubbles provide a seed for cavitation which induces the formation of larger bubbles.

When such contrast agent is used, higher power ultrasonic signals can be applied to cause the contrast agent to become more echogenic rather than less echogenic. In this case, the lower power imaging ultrasonic signals will show enhanced reflection from the regions of contrast agent that were subjected to the higher power ultrasonic signals. In this case, the higher power ultrasonic signal can be said to activate the contrast agent in order to render it more echogenic, or operative. Any of the methods and systems discussed above can be used with contrast agent that is activated rather than disrupted by high power ultrasonic signals.

As used herein, a set of ultrasound signals includes signals associated with one or more transmit events that create a region of disrupted contrast agent or a region of activated contrast agent (in the case of the first transducer or transducer array) or that provide an image of a selected region of the vessel (in the case of the second transducer array).

The term "vessel" is intended broadly to include both generally tubular vessels such as arteries, veins, and capillaries, as well as vessels of other shapes such as heart chambers.

As used herein, operative contrast agent signifies contrast agent that is effective to return an enhanced echo signal, either at the fundamental or the harmonic frequency. Disrupted contrast agent signifies contrast agent that has been destroyed or otherwise modified such that it returns a substantially reduced or negligible echo signal.

The term "selectively transmitting" at a frequency means to transmit ultrasonic power at and near the stated frequency while suppressing ultrasonic power at harmonic frequencies. The term "selectively receiving" is used to indicate that only selected components of the received echo signal are processed, while other components (at the fundamental frequency for example) are suppressed or rejected.

The term "duty cycle" as applied to high intensity ultrasound signals used to disrupt or activate contrast agent refers to the fraction of the total time during which such signals are actively generated. Typically, a single active period will include a plurality of discrete acoustic lines, and there may well be dead time between lines. In this case, duty cycle refers to the time period of frames of acoustic lines used to disrupt or activate contrast agent as a fraction of the total time period.

The foregoing detailed description has described only a few of the many forms of the present invention can take. For example, though the foregoing discussion has referred to second harmonic non-linear contrast agent, this invention can also be used with conventional non-harmonic contrast agents in cases where sufficient power can be employed to destroy these contrast agents without exceeding regulatory limits. Also the higher and lower power transmit events may be interleaved on a line-by-line basis, group-of-lines by group-of-lines basis, frame-by-frame basis, or group-of-frames by group-of-frames basis.

As another example, it is not required in all embodiments that higher and lower power transmit events alternate. Rather, it is possible that higher power transmit events be produced completely asynchronously with respect to lower power transmit events. This can be done for example by using two discrete transmitting circuits which act independently of one another.

It should be understood that it Is not required in all cases that the high intensity ultrasound signals alternate in a binary fashion between an on and an off state. Alternately, the intensity of the ultrasound signals can vary continuously, as for example sinusoidally. Due to the non-linear effects encountered with contrast agent, an approximately binary output may still result.

It is therefore intended that the foregoing detailed description be regarded as illustrative rather than limiting. It is only the following claims, including all equivalents, that are intended to define the scope of this invention.

I claim:

1. An ultrasonic method for assessing flow characteristics in a vessel, said vessel comprising blood and a contrast agent, said method comprising the following steps:
    (a) transmitting sets of higher power ultrasonic signals into a first region of the vessel, said higher power ultrasonic signals operative to selectively disrupt the contrast agent in said first region of the vessel, to create a volume of blood in the vessel characterized by a reduced concentration of operative contrast agent; and
    (b) imaging the contrast agent in a second region of the vessel, said second region including additional portions of the vessel not included in the first region and positioned downstream of the first region, said imaging step comprising the step of
        (b1) transmitting lower power ultrasonic signals into the second region of the vessel, said lower power ultrasonic signals disrupting the contrast agent to a lesser extent than said higher power ultrasonic signals.

2. The method of claim 1 wherein step (a) comprises the step of shaping the first region in a selected form corresponding substantially to a plurality of planes.

3. The method of claim 1 wherein step (a) comprises the step of shaping the first region in a selected form corresponding substantially to a plurality of intersecting planes.

4. An ultrasonic method for assessing flow characteristics in a vessel, said vessel comprising blood and a contrast agent, said method comprising the following steps:
    (a) transmitting sets of higher power ultrasonic signals into a first region of the vessel, said higher power ultrasonic signals operative to selectively activate the contrast agent in said first region of the vessel, to create a volume of blood in the vessel characterized by an enhanced concentration of operative contrast agent; and
    (b) imaging the contrast agent in a second region of the vessel, said second region including additional portions of the vessel not included in the first region and positioned downstream of the first region, said imaging step comprising the step of
        (b1) transmitting lower power ultrasonic signals into the second region of the vessel, said lower power ultrasonic signals activating the contrast agent to a lesser extent than said higher power ultrasonic signals.

5. The method of claim 1 or 4 wherein step (a) comprises the step of applying a plurality of first transmit waveforms to a first transducer, wherein step (b1) comprises the step of applying a plurality of second transmit waveforms to a second transducer.

6. The method of claim 5 wherein the first transducer is oriented substantially perpendicular to the second transducer.

7. The method of claim 5 wherein at least one of the first and second transducers comprise a respective transducer array.

8. The method of claim 1 or 4 wherein the higher and lower power ultrasonic signals are positioned within a single frame, and wherein the higher power ultrasonic signals are positioned near a first edge of the frame.

9. The method of claim 1 or 4 wherein step (b1) comprises the step of selectively transmitting the lower power ultrasonic signals concentrated near a fundamental frequency; wherein step (b) further comprises the step of (b2) selectively receiving ultrasonic signals concentrated near a harmonic of the fundamental frequency; and wherein the contrast agent comprises a non-linear contrast agent.

10. The method of claim 1 or 4 comprising the further step of
    (c) using the contrast agent imaging of step (b) to assess blood flow velocity.

11. The method of claim 10 wherein step (c) comprises the step of providing a user-positioned caliper to mark regions of disrupted contrast agent.

12. The method of claim 10 wherein step (c) comprises the steps of
    (c1) creating a profile of imaged contrast agent, said profile extending through a plurality of regions of disrupted contrast agent; and
    (c2) analyzing the profile to automatically determine a separation between two regions of disrupted contrast agent.

13. The method of claim 1 or 4 comprising the further step of
    (c) using the contrast agent imaging of step (b) to assess a blood flow profile across the vessel.

14. The method of claim 1 or 4 comprising the further step of
    (c) using the contrast agent imaging of step (b) to assess blood flow turbulence.

15. The method of claim 1 or 4 comprising the further step of
    (c) using the contrast imaging of step (b) to assess blood flow per heart beat cycle.

16. The method of claim 1 or 4 wherein step (a) comprises the step of varying a power level characteristic of the higher power ultrasonic signals in response to a user-controlled adjustment.

17. The method of claim 1 or 4 wherein step (a) comprises the step of varying a time interval between consecutive sets of said higher power ultrasonic signals in response to a user-controlled adjustment.

18. The method of claim 1 or 4 wherein step (a) comprises the step of varying a width of a spatial distribution of the higher power ultrasonic signals in response to a user-controlled adjustment.

19. The method of claim 1 or 4 wherein at least selected sets of the higher power ultrasonic signals sweep the first region of the vessel multiple times per set.

20. The method of claim 1 or 4 wherein at least selected sets of the higher power ultrasonic signals include first higher power ultrasonic signals focused at a first range and second higher power ultrasonic signals focused at a second range, different from the first range.

21. The method of claim 1 or 4 wherein step (a) comprises the step of synchronizing at least some of the sets of higher power ultrasonic signals with a selected portion of an EKG signal.

22. The method of claim 3 wherein the selected form is V-shaped.

23. The method of claim 3 wherein the selected form is X-shaped.

24. The method of claim 1 or 4 wherein step (a) is characterized by a duty cycle, and wherein the duty cycle of step (a) is greater than 50%.

25. The method of claim 1 or 4 wherein step (a) is characterized by a duty cycle, and wherein the duty cycle of step (a) is less than 50%.

* * * * *

UNITED STATES PATENT AND TRADEMARK OFFICE
CERTIFICATE OF CORRECTION

PATENT NO. : 5,944,666
DATED : August 31, 1999
INVENTOR(S) : John A. Hossack et al.

It is certified that error appears in the above-identified patent and that said Letters Patent is hereby corrected as shown below:

On the Title Page

Page 2, column 2, line 17, please change "1'Jun." to --1-Jun.--.

Page 2, column 2, line 47, please change "Time domain" to --Time-domain--.

Page 2, column 2, line 58, please change "frpm" to --from--.

Signed and Sealed this

Tenth Day of April, 2001

Attest:

NICHOLAS P. GODICI

*Attesting Officer*   *Acting Director of the United States Patent and Trademark Office*